United States Patent
Jiang

(10) Patent No.: US 9,575,008 B2
(45) Date of Patent: Feb. 21, 2017

(54) APPARATUS AND METHOD FOR PHOTOGRAPHING GLASS IN MULTIPLE LAYERS

(71) Applicant: ASA Corporation, Rocklin, CA (US)

(72) Inventor: Liansheng Jiang, Rocklin, CA (US)

( * ) Notice: Subject to any disclaimer, the term of this patent is extended or adjusted under 35 U.S.C. 154(b) by 328 days.

(21) Appl. No.: 14/178,295

(22) Filed: Feb. 12, 2014

(65) Prior Publication Data
US 2015/0226675 A1     Aug. 13, 2015

(51) Int. Cl.
*G01N 21/88* (2006.01)
*G01N 21/958* (2006.01)
*G01N 33/38* (2006.01)

(52) U.S. Cl.
CPC ........ *G01N 21/8806* (2013.01); *G01N 21/958* (2013.01); *G01N 33/386* (2013.01); *G01N 2201/02* (2013.01); *G01N 2201/062* (2013.01)

(58) Field of Classification Search
CPC  G01N 21/8806; G01N 21/958; G01N 33/386; G01N 2201/02; G01N 2201/062; G01N 21/8809
See application file for complete search history.

(56) References Cited

U.S. PATENT DOCUMENTS

| | | | |
|---|---|---|---|
| 4,253,768 A * | 3/1981 | Yaroshuk | G01N 21/89 250/559.39 |
| 4,874,940 A * | 10/1989 | McMeekin | G01N 21/9018 250/223 B |
| 5,087,822 A * | 2/1992 | Fairlie | G01N 21/8903 250/559.16 |
| 6,148,097 A * | 11/2000 | Nakayama | G01M 11/0278 382/141 |
| 6,201,600 B1 * | 3/2001 | Sites | G01M 11/0264 356/124 |
| 6,429,943 B1 * | 8/2002 | Opsal | G01B 11/02 356/625 |
| 6,598,994 B1 * | 7/2003 | Tait | G01B 11/00 362/11 |
| 7,215,736 B1 * | 5/2007 | Wang | G01N 23/046 378/21 |
| 7,804,248 B1 * | 9/2010 | Li | H01J 61/30 313/631 |
| 8,064,072 B2 * | 11/2011 | Schmitt | G01B 11/0691 356/625 |
| 2001/0002862 A1 * | 6/2001 | Okahira | G01N 21/958 356/237.1 |
| 2002/0139919 A1 * | 10/2002 | Sardana | G01D 5/35383 250/208.1 |

(Continued)

FOREIGN PATENT DOCUMENTS

JP     2008076218 A  *  4/2008

*Primary Examiner* — Jay Patel
*Assistant Examiner* — Joseph Suh
(74) *Attorney, Agent, or Firm* — Dahyee Law Group; Leon E. Jew; Lin Kong

(57) ABSTRACT

The invention teaches a new apparatus and method to photograph glasses in multiple layers for taking high quality photo images with scratch, crash, black/white defect, lack, crack, pin-hole, concave edge and raised edge, bubble and smudge defects on the surface-layer, backside-layer or/and mid-layer of the glasses. The invention also introduces flexible and expendable photographing hardware architecture that will meet various customers inspecting defects requirements and speed requirements.

1 Claim, 10 Drawing Sheets

(56) References Cited

U.S. PATENT DOCUMENTS

| | | | |
|---|---|---|---|
| 2002/0154295 A1* | 10/2002 | Ivakhnenko | G01N 15/0211 356/237.2 |
| 2003/0101885 A1* | 6/2003 | Jordan | B41F 27/1275 101/395 |
| 2003/0118249 A1* | 6/2003 | Edgar | G06T 7/0002 382/275 |
| 2004/0032581 A1* | 2/2004 | Nikoonahad | G01N 21/9501 356/237.2 |
| 2004/0174540 A1* | 9/2004 | Saito | G01B 11/2513 356/612 |
| 2005/0029461 A1* | 2/2005 | Malmin | G01T 1/1644 250/367 |
| 2006/0008133 A1* | 1/2006 | Dordoni | G01N 21/8851 382/142 |
| 2006/0109454 A1* | 5/2006 | Engelbart | G01N 21/89 356/237.1 |
| 2006/0159330 A1* | 7/2006 | Sakai | G06T 7/001 382/141 |
| 2006/0215898 A1* | 9/2006 | Song | G01N 21/8806 382/141 |
| 2006/0238753 A1* | 10/2006 | Tsuji | G01N 21/8803 356/237.2 |
| 2006/0290647 A1* | 12/2006 | Oron | B60K 37/00 345/102 |
| 2008/0079933 A1* | 4/2008 | Fukami | G01N 21/954 356/237.2 |
| 2008/0186481 A1* | 8/2008 | Chen | G01N 21/8806 356/237.1 |
| 2008/0312747 A1* | 12/2008 | Cameron | A61F 2/91 623/23.7 |
| 2009/0141965 A1* | 6/2009 | Ferlay | G01N 21/952 382/152 |
| 2009/0233811 A1* | 9/2009 | Bota | B01J 19/0046 506/16 |
| 2009/0257058 A1* | 10/2009 | Urano | G01N 21/9503 356/364 |
| 2009/0310239 A1* | 12/2009 | Adler | G01N 21/8806 359/891 |
| 2010/0045807 A1* | 2/2010 | Mizuta | G01N 21/8806 348/216.1 |
| 2010/0051834 A1* | 3/2010 | Lopatin | G01N 21/896 250/553 |
| 2011/0016975 A1* | 1/2011 | Glaesemann | G01N 29/043 73/588 |
| 2011/0141272 A1* | 6/2011 | Uto | G01N 21/9501 348/135 |
| 2011/0286052 A1* | 11/2011 | Takabatake | H04N 1/00395 358/475 |
| 2012/0014820 A1* | 1/2012 | Mardilovich | H01L 41/23 417/410.2 |
| 2012/0092484 A1* | 4/2012 | Taniguchi | G01N 21/956 348/87 |
| 2012/0111115 A1* | 5/2012 | Ume | G01N 29/2418 73/588 |
| 2013/0076871 A1* | 3/2013 | Reeves | G01B 11/2518 348/50 |
| 2013/0128026 A1* | 5/2013 | Hirose | G01N 21/8903 348/125 |
| 2015/0077538 A1* | 3/2015 | Krebs | G01N 21/8803 348/88 |

* cited by examiner

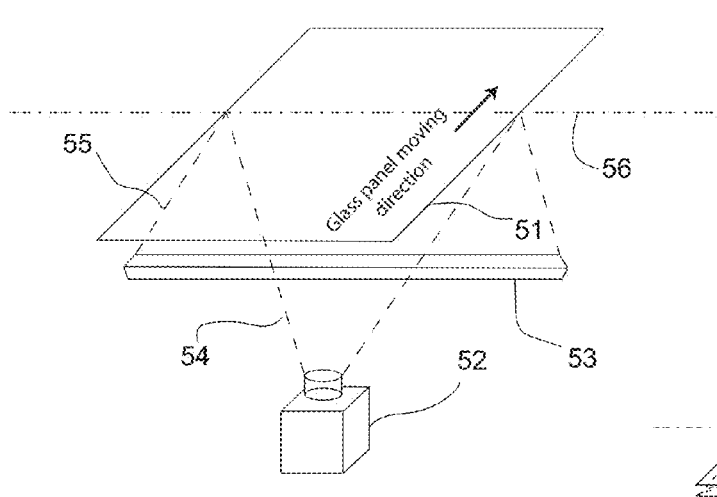
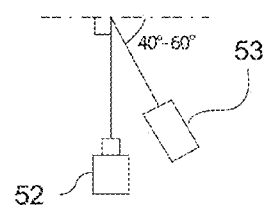
FIG. 5-2
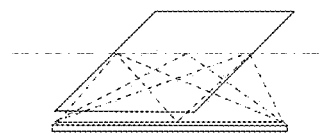
FIG. 5-1
FIG. 5-3

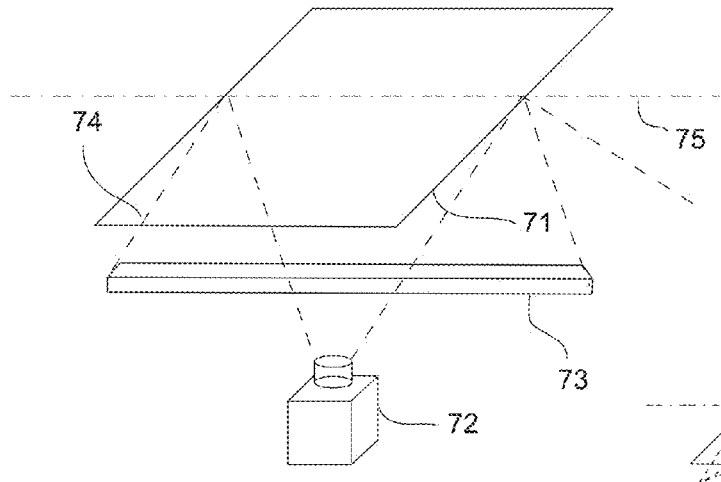
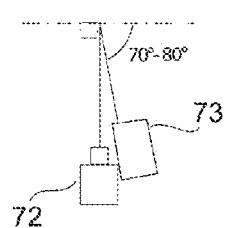
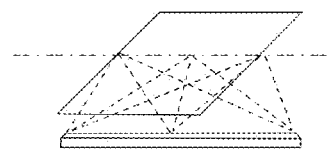
FIG. 7-1
FIG. 7-2
FIG. 7-3

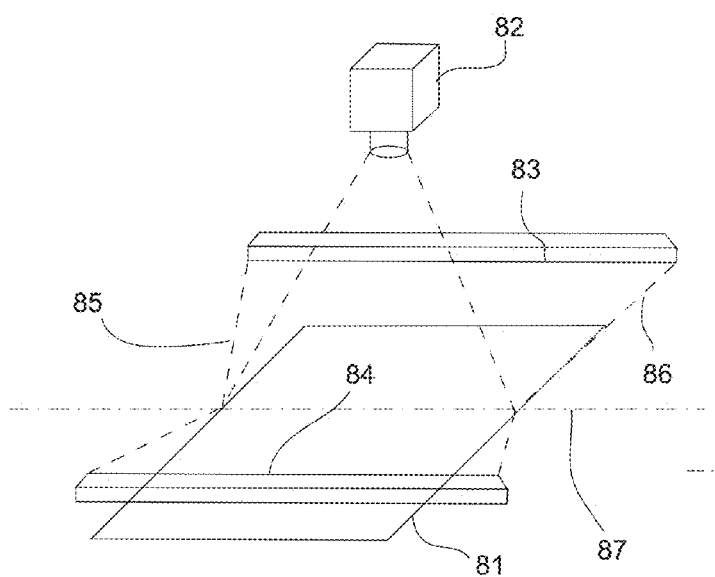
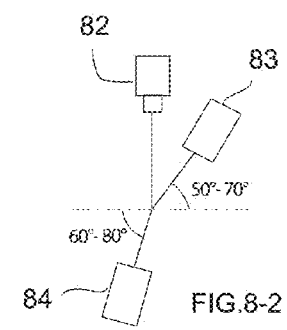
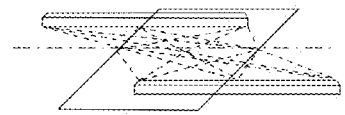
FIG. 8-1
FIG. 8-2
FIG. 8-3

APPARATUS AND METHOD FOR PHOTOGRAPHING GLASS IN MULTIPLE LAYERS

CROSS REFERENCE TO RELATED APPLICATIONS

This application is a continuation-in-part of, and claims the benefit of priority to, the PCT application No. PCT/CN2012/074463 that further claimed the priority benefit to the U.S. Provisional Application No. 61/517,620, the content of which is incorporated in its entirety by reference herein.

FIELD OF THE INVENTION

The present invention generally relates to the field of glass inspection which requests to photograph different defects (such as scratches, crashes, black/white defects, lack, cracks, pin-holes, concave edges and raised edges, bubbles and smudges) on the surface, backside and mid-layer of glasses in high accuracy. More particularly, the invention is a consistent, stable, fast, and high accuracy glass photographing apparatus, and the method for creating the same. The technology of present invention relates to the field of machine-vision applications, involves motion control, optical, photography design, and apparatus hardware architecture. Especially, this invention introduces a multiple camera process when each camera will take one full image for inspecting one or more defect(s) on multiple glass layer(s).

BACKGROUND OF THE INVENTION

Glass inspection is applied in many fields, especially in the field of mobile phone display panel, iPad window panel and flat-panel display manufactures. Due to difficultly for taking high quality images on different defects (scratches, crashes, black/white defects, lack, cracks, pin-holes, concave edges and raised edges, bubbles and smudges) on the surface, backside and mid-layer of glasses, therefore in the world, no full automatic glass inspection system provides high quality inspection solution, thus the method of human manual inspections is still used in most glass manufactures. The inspection accuracy of this method is limited by the vision of human beings and the inspection results of this method can become not reliable due to human errors from human's feeling, emotion and tiredness.

Among the current automatic glass detection technology, there are some apparatus that can photograph one or several defects, but it still lacks a consistent, stable, fast, and high accuracy glass photographing apparatus, and the method for creating the same.

Among the current automatic glass detection technology, most of glass photography devices use multiple area scanning cameras for high accuracy photography, but this technique is restricted at its mechanical mounting space when photographing small size glasses such as mobile phone glass panel. This invention uses multiple line-scanning cameras with micro-lens to walk around the problem of space limit.

Among the multiple layer glass photography of the invention, multiple layer photography for scratches on glasses is most difficult. So far there is no single apparatus that can photograph glass scratches at all orientations. For instance, one apparatus is able to take clear photographs to expose scratches on glasses on vertical direction (+/+30°) but not on horizon direction, and another apparatus is able to take clear scratch photographs on glasses on horizon direction (+/−30°) but not on vertical direction. To solve the glass photograph problem that it is difficult to get clear photographs to expose scratches on all orientations, this invention introduces an apparatus that adopts an illumination technology using multiple lights to spread on the glass from different positions and various angles.

Most of machine-vision applications take one photograph of glass panel for image process and inspection. The apparatus of this invention introduces flexible hardware architectures. Using the apparatus of this invention, it can take one or multiple photo-images for each glass panel based on the glass inspection need of customer, and each photo-image can capture clear image of one or more defects in various layers. This results in fast inspections of multiple-layered glass with the support of multi-tasking image process and inspection.

On normal machine vision applications, the photographing hardware is usually fixed, and is not easy to modify. This invention introduces a flexible hardware architectures for various glass inspecting purposes.

There are two methods to take photo-image on glasses. One is fixing glasses and move cameras, and the other is fixing cameras and moving glasses. The later method is used in this invention.

To control photographing and real-time inspection at multiple glass layers, multi-tasking photographing, image processing and inspection techniques software must be programmed.

SUMMARY OF THE INVENTION

This invention involves an apparatus and method thereof for photographing defects (scratches, crashes, black/white defects, lack, cracks, pin-holes, concave edges and raised edges, bubbles and smudges) on multiple layers of glasses. The apparatus contains the following hardware components: a conveyor, one or more line-scan or area-scan camera(s), one or more line-light(s) or area-light(s), and one or more normal lens or micro-lens.

This invention introduces an apparatus and method thereof to get clear photographs to expose scratches on a glass panel by using multiple lights that spread line beams from different positions and angles. The line-scan camera is mounted vertically with the glass panel, and two line-lights are mounted in parallel to the camera's scan-line and spread the first two line beams on the camera's scan-line, another two line-lights spread two line beams from both sides of camera, merging with the first two line beams on the camera's scan line. This technique is able to get clear photographs to expose scratches on all orientations.

This invention introduces an apparatus and method thereof to get clear photographs to expose silk print defects on a glass panel. A line-scan camera is mounted on the topside of the glass panel and is vertical with the glass panel, one line-light is mounted in parallel to the camera's scan-line and spreads the line beam on the camera's scan-line on the surface of the glass panel. This technique is able to get clear photographs to expose silk print defects.

This invention introduces an apparatus and method thereof to get clear photographs to expose black/white defects: A line-scan camera is mounted above the glass panel and is vertical to the glass panel, two line-lights are mounted above the glass panel and spread line beams on the camera's scan-line from above the glass panels. This technique is able to get clear photographs to expose black/white defects.

This invention introduces an apparatus and method thereof to get clear photographs to expose side-crash or lack defects: A line-scan camera is mounted above the glass panel and is vertical to the glass panel, one line-light is mounted at backside of the glass panel and spreads a line beam on the camera's scan-line on the backside of the glass panel. This technique is able to get clear photographs to expose side-crash or lack defects.

This invention introduces an apparatus and method thereof to get clear photographs to expose cracks defects: A line-scan camera is mounted at back side of the glass panel and is vertical to the glass panel, one line-light is mounted at backside of the glass panel and spreads a line beam on the camera's scan-line on the backside of the glass panel. This technique is able to get clear photographs to expose cracks defects.

This invention introduces an apparatus and method thereof to get clear photographs to expose pin-hole defects: A line-scan camera is mounted above the glass panel and is vertical to the glass panel, two line-lights are mounted at backside of a glass panel and spread line beams on the camera's scan-line on the backside of the glass panel. This technique is able to get clear photographs to expose pin-hole defects.

This invention introduces an apparatus and method thereof to get clear photographs of concave edges and raised edges to expose defects: A line-scan camera is mounted above the glass panel and is vertical to the glass panel, one line-light is mounted at backside of the glass panel and spreads a line beam on the camera's scan-line on the backside of the glass panel. This technique is able to get clear photographs of concave edges and raised edges to expose defects.

This invention introduces an apparatus and method thereof to get clear photographs of bubble and/or smudge to expose defects: A line-scan camera is mounted above the glass panel and is vertical to the glass panel, two line-lights are mounted on the topside and on the backside of the glass panel respectively and spread line beams on the camera's scan-line. This technique is able to get clear photographs of bubble and/or smudge to expose defects.

This invention introduces flexible hardware architectures for various glass inspecting purposes. Depending on total types of inspecting glass defects from the individual customer required, various hardware systems can be designed by mounting multiple cameras and line-lights, and each camera will photograph one or more defects on the glass. In such kind of customized hardware system, all spots of glass defects that are required to inspect by a customer will be photographed.

BRIEF DESCRIPTION OF THE DRAWINGS

All schematic diagrams included in this invention do not contain distances between the cameras and the glass panels since the distances depend on (1) Resolution of line-scan camera, for instance 1K, 2K, 4K, 8K, 12K or 16K line-scan cameras or larger scale area-scan cameras are popular in machine vision applications, (2) Width of glasses, and (3) Defects inspection accuracy requirements. Any selection of them will result in varies of distances between the cameras and the glass panels.

FIG. 1-1 is a schematic diagram of the invention for exposing scratches on the surface or backside of glasses.

FIG. 1-2 is a schematic diagram illustrating the conjunction angle between camera's scan-line and line-lights according to FIG. 1-1.

FIG. 1-3 is a schematic illustrating the merged light beams that spread on the camera's scan line according to FIG. 1-1.

FIG. 2-1 is a schematic diagram of the invention for exposing silk print defects on the glasses.

FIG. 2-2 is a schematic diagram illustrating the conjunction angle between camera's scan-line and the line-light according to FIG. 2-1.

FIG. 2-3 is a schematic diagram of FIG. 2-1 illustrating the light beam that spreads on the camera's scan-line according to FIG. 2-1.

FIG. 3-1 is a schematic diagram of the invention for exposing black/white defects on the glasses.

FIG. 3-2 is a schematic diagram illustrating the conjunction angle between camera's scan-line and line-lights according to FIG. 3-1.

FIG. 3-3 is a schematic diagram showing the light beams that spread on the camera's scan-line according to FIG. 3-1.

FIG. 4-1 is a schematic diagram of the invention for exposing side-crash and lack defects on the glasses.

FIG. 4-2 is a schematic diagram illustrating the conjunction angle between camera's scan-line and the line-light according to FIG. 4-1.

FIG. 4-3 is a schematic diagram illustrating the light beam that spreads on the camera's scan-line according to FIG. 4-1.

FIG. 5-1 is a schematic diagram of the invention for exposing cracks on the glasses.

FIG. 5-2 is a schematic diagram illustrating the conjunction angle between camera's scan-line and the line-light according to FIG. 5-1.

FIG. 5-3 is additional schematic diagram of FIG. 5-1 to show the light beam that spreads on the camera's scan-line according to FIG. 5-1.

FIG. 6-1 is a schematic diagram of the current invention for exposing pin-holes on the glasses.

FIG. 6-2 is a schematic diagram illustrating the conjunction angle between camera's scan-line and line-lights according to FIG. 6-1.

FIG. 6-3 is a schematic diagram illustrating the light beams that spread on the camera's scan-line according to FIG. 6-1.

FIG. 7-1 is a schematic diagram of the invention for exposing concave edges and raised edges on the glasses.

FIG. 7-2 is a schematic diagram illustrating the conjunction angle between camera's scan-line and the line-light according to FIG. 7-1.

FIG. 7-3 is a schematic diagram illustrating the light beam that spreads on the camera's scan-line according to FIG. 7-1.

FIG. 8-1 is a schematic diagram of the invention for exposing bubbles and smudges on the glasses.

FIG. 8-2 is a schematic diagram illustrating the conjunction angle between camera's scan-line and line-lights according to FIG. 8-1.

FIG. 8-3 is a schematic diagram illustrating the lighting beams that spread on the camera's scan-line according to FIG. 8-1.

DESCRIPTION OF THE INVENTION

This invention introduces an apparatus for photographing the defects including but not limit to scratches, cracks, concave and raised edges, bubbles and smudges on the surface, backside and mid-layer of glass(es). The mechanism of the apparatus associated with photography involves a conveyor, one or more line-scan or area-scan camera(s), one or more line-light(s) or area-light(s), and one or more normal lens (for low accuracy) or micro-lens (for high accuracy) depending on accuracy of inspection requirements. The conveyor can be roller conveyor, air floating conveyor or any other type of conveyor; the selected conveyor for line-scan camera must leave enough gaps for line-scanning; the light source is a strip-shaped light source made of LED lights or other type of lights, including strip-shaped line-light source or strip-shaped area-light source; the lens is the normal lens or micro-lens; and the computer is for devices (conveyor, camera, lighting source) controls and for glass image acquisitions. Since the techniques of conveyor, camera and lens is beyond this invention, they will not be described more in details.

Figure 9:
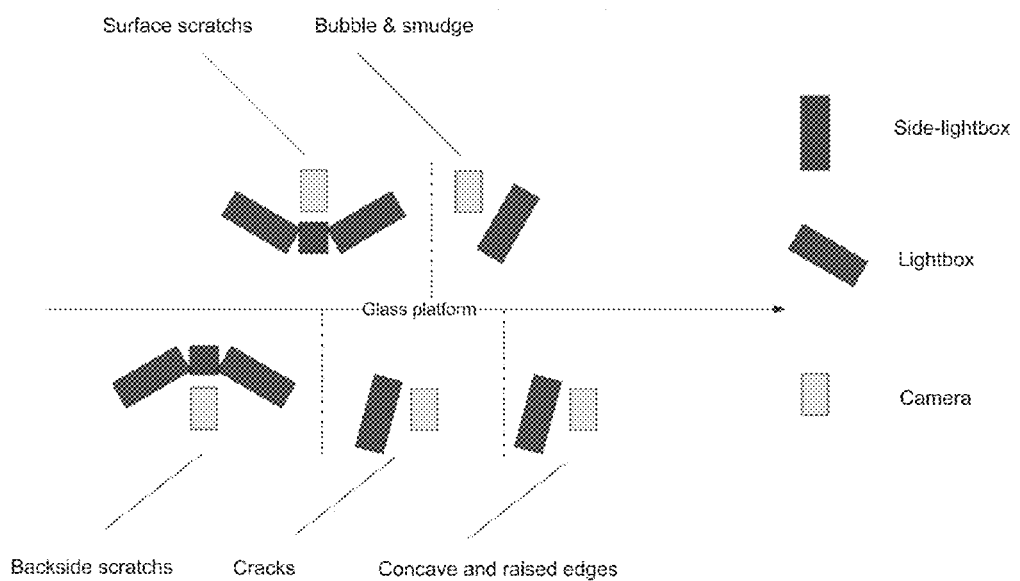
FIG. 9 is a sample device hardware architecture schematic diagram, which photographs the mobile phone glasses before the silk printing.

This invention also introduces flexible and expendable photographing hardware architectures according to customer inspecting defects requirements and speed requirements. For instance, to inspect the mobile phone glasses before silk-printing, the requested photographing spots of defects include scratches, cracks, concave and raised edges, bubbles and smudges on the surface, backside and mid-layer of glasses. To construct such kind of inspection system, we set two line-scan cameras and six line-lights for exposing scratches on surface and backside of glasses, another three line-scan cameras and three line-lights shall be involved for exposing cracks, concave and raised edges, bubbles and smudges. FIG. 9 is a schematic diagram illustrating a sample hardware configuration for exposing mobile phone glass before silk printing. The iPad front panel glass inspection shall be constructed the same way for photography.

Figure 10:
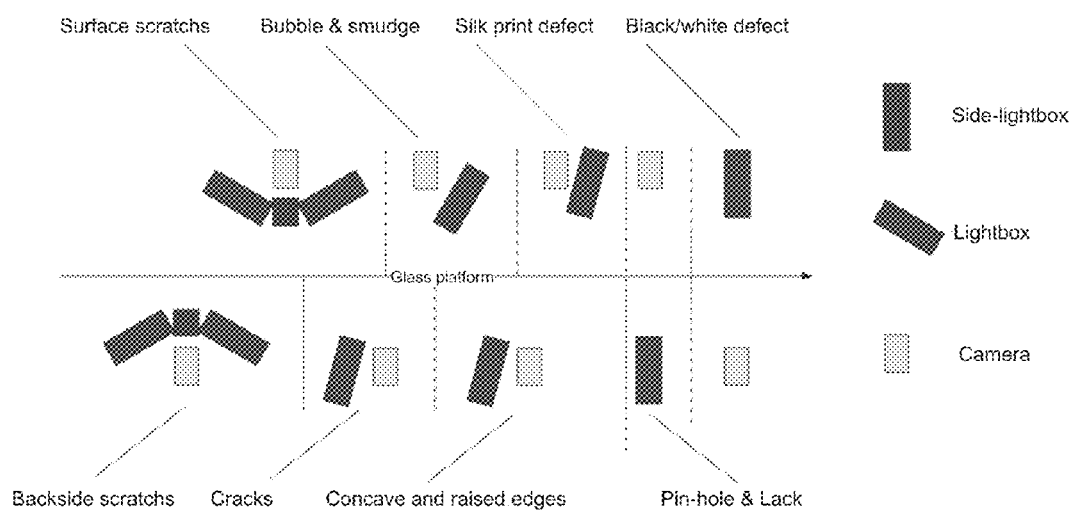
FIG. 10 is a sample device hardware architecture schematic diagram, which photographs the mobile phone glasses after the silk printing.

As another instance, after silk-printing, the mobile phone glass maker will request to photograph spots to expose defects include scratches, silk print defect, black/white defects, lack, cracks, pin-holes, concave and raised edges, bubbles and smudges on the surface, backside and mid-layer of glasses. This comprehensive inspection will request up to eight line-scan cameras and twelve line-lights. Mainly more cameras and line-lights will raise the productivities of the glass inspection. FIG. 10 is a schematic diagram illustrating a sample hardware configuration for inspecting mobile phone glass after silk printing.

Figures 1, 2, 3:
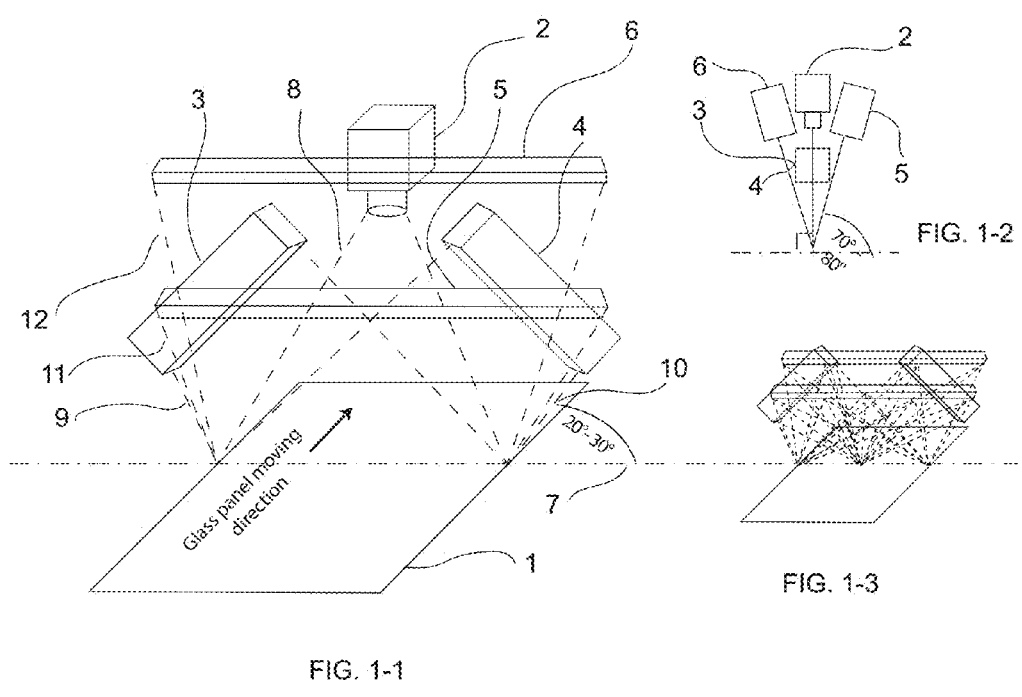
Figures 1, 2, 3:
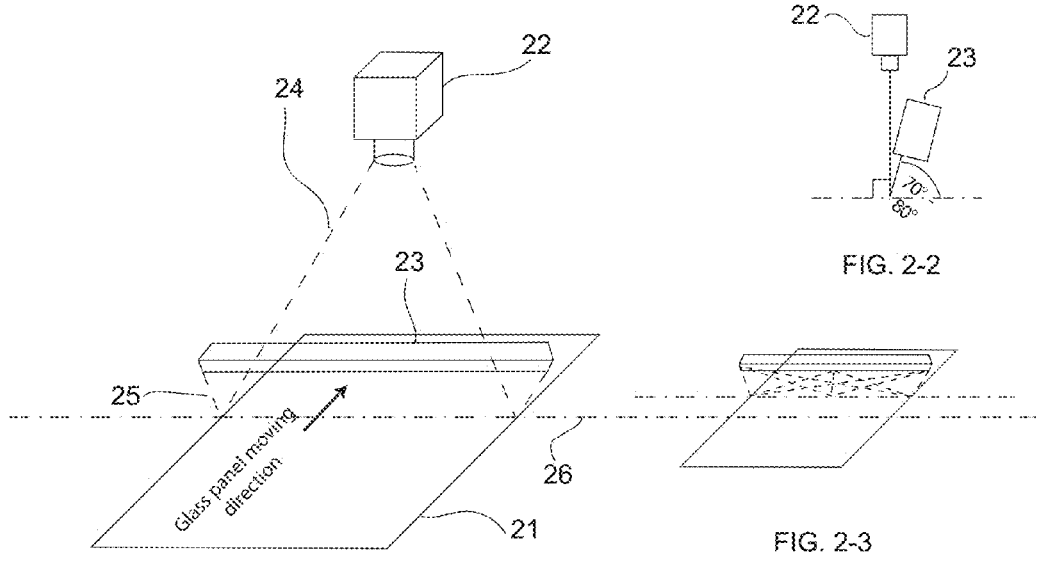
Figures 1, 3:
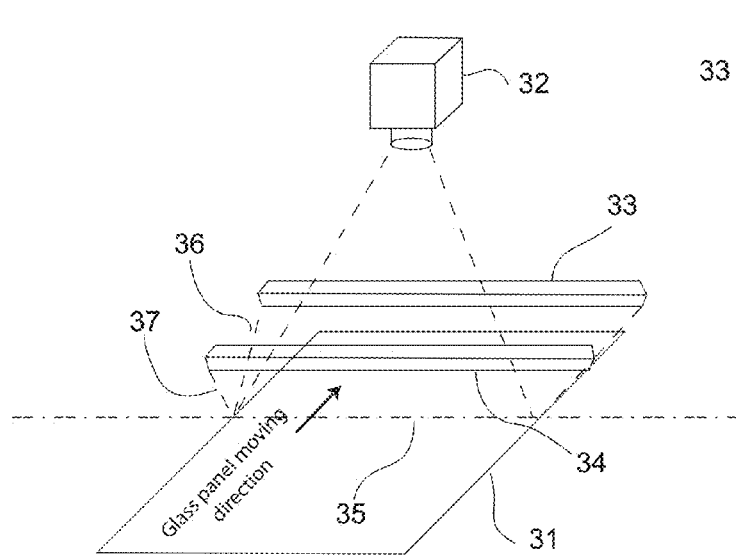
Figures 2, 3:
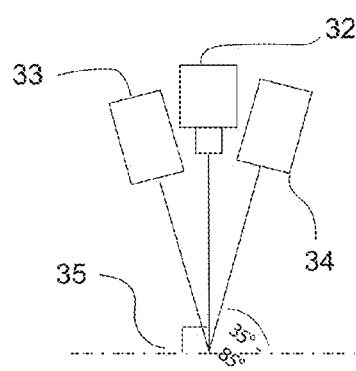
Figure 3:
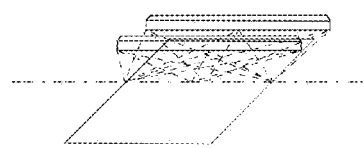

This invention introduces an apparatus and method thereof to get clear scratch(es) photographs using multiple lights spread from different positions and angles. FIG. 1-1 is a schematic diagram illustrating the hardware configuration for scratch inspection according to the present invention, and FIG. 1-2 is a schematic diagram illustrating the camera-light angle is 70°~80° according to FIG. 1-1. The line-lights (5 & 6) spread the first two line beams on the camera's scan-line (7), another two line-lights (3 & 4) spread two line beams (9 & 10) from both sides of the camera (2), the angle of line beams (9 & 10) and camera's scan-line (7) is about 20°~30° for exposing the scratches in +/−30° of orientation from glass panel moving direction. This structure of line-lights (3, 4, 5 & 6) results in spreading and merging the line beams (9, 10, 11 & 12) on the entire camera's scan-line (7). FIG. 1-3 is an optical path diagram illustrating how three points (left-edge-point, mid-point and right-edge-point) on camera's scan line (7) are illuminated by lights in many directions from line-lights (3, 4, 5 & 6) as shown in FIG. 1-1. Obviously any point on camera's scan line (7) will be spread by lights from various directions from the line-lights (3, 4, 5 & 6), it will guarantee all the scratches (in any orientation) be exposed when the line-scan camera (2) photographs line by line and make a clear scratch picture. Without line-lights (3 and/or 4) in FIG. 1, it is not able to expose scratches in +/−30° of orientation from glass panel moving direction; and without line-lights (5 & 6) in FIG. 1, it is not able to expose scratches in +/−30° of orientation from camera's scan-line (7). In FIG. 1-2, why the camera and light-beam angle is about 70°~80°? Because keeping the line-light (5 & 6) enough vertically will make the line beams (11 & 12) spreading deeply into scratches for exposing deeper scratches.

This invention introduces an apparatus and method thereof to get clear silk print defect photographs using one line-light. FIG. 2-1 is a schematic diagram illustrating the hardware configuration for silk print defect inspection apparatus according to the present invention. FIG. 2-2 is a schematic diagram illustrating the camera-light angle according to FIG. 2-1. FIG. 2-3 is an optical path diagram illustrating how three points (left-edge-point, mid-point and right-edge-point) on camera's scan-line (26) are illuminated by lights in many directions from line-light (23) as shown in FIG. 2-1. Obviously any point on camera's scan-line (26) will be spread by lights from various directions from the line-lights (23), it will guarantee all the silk print defects (in any orientation) be exposed when the line-scan camera (22) photographs line by line and make a clear silk print defect picture. In FIG. 2-2, why the camera and light-beam angle is about 70°~80°. It is because keeping the line-light (23) enough vertically will make the line beam (25) spreading deeply since the silk printing material is thicker relatively in micro-photographing.

This invention introduces an apparatus and method thereof to get clear black/white defect photographs using two line-lights. FIG. 3-1 is a schematic diagram illustrating the hardware configuration for black/white defects inspection apparatus to the present invention; and FIG. 3-2 is a schematic diagram illustrating angle between the glass and the light beams is 35°~85° according to FIG. 3-1. The line-scan camera (32) is mounted on the top of glass panel (31) vertically with the glass panel (31), and two line-lights (33 & 34) are mounted on the top side of glass panel in parallel with camera's scan-line (35), and spread light beams (36 & 37) on the camera's scan-line (35). FIG. 3-3 is an optical path diagram illustrating how three points (left-edge-point, mid-point and right-edge-point) on camera's scan-line (35) are illuminated by lights in many directions from line-light (33) as shown in FIG. 3-1. Obviously any point on camera's scan-line (35) will be spread by lights from various directions from the line-lights (33 & 34), when the light beams (36 & 37) pass through the glass panel (31), the black/white defects will block the part of light beams (36 & 37), different defect's color (black or white) or layer will result in various shape and gray-scale on the photograph. Therefore, all the black/white defects will pass through the light beams (36 & 37) and be exposed. And the line-scan camera (32) photographs line by line and makes a clear black/white defects picture.

Figures 1, 2, 3, 4:
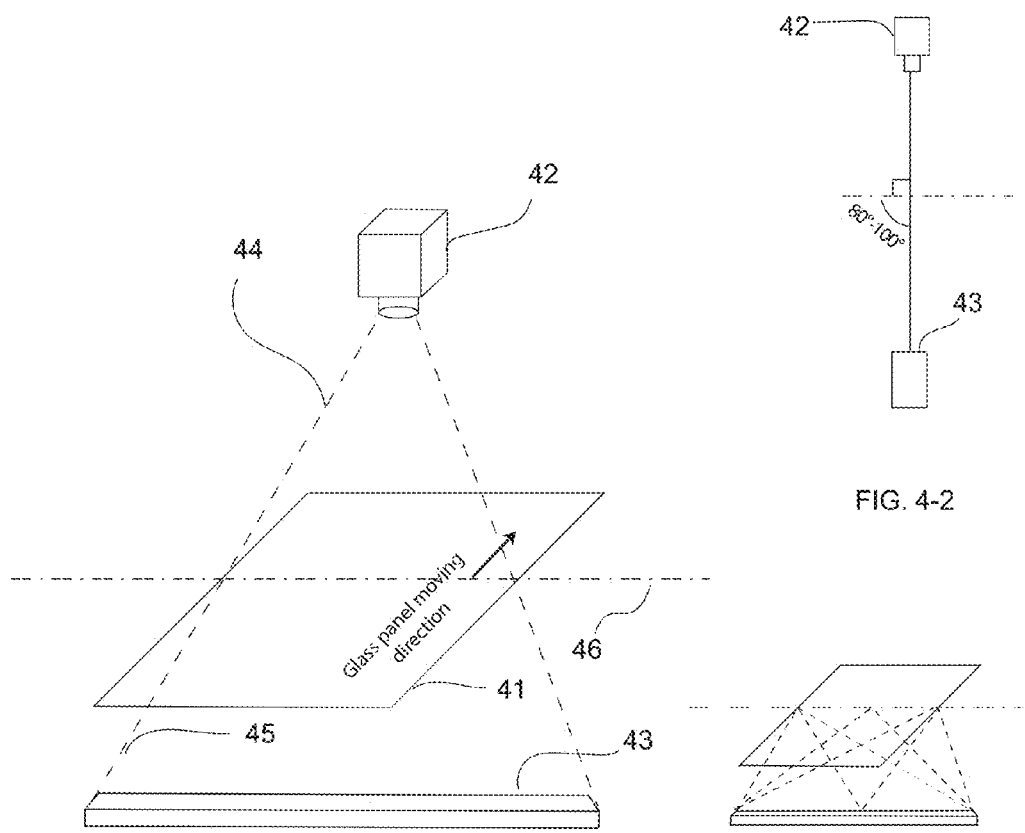

This invention introduces an apparatus and method thereof to get clear side-crash and lacks photographs using one line-light. FIG. 4-1 is a schematic diagram illustrating the hardware configuration for lacks inspection apparatus according to the present invention and FIG. 4-2 is a schematic diagram illustrating the angle between the glass and the light beam is 80°~100° according to FIG. 4-1. The line-scan camera (42) is mounted on the top of glass panel (41) vertically with the glass panel (41), and one line-light (43) is mounted on the backside of glass panel in parallel with camera's scan-line (46), and spreads light beam (45) with the camera's scan-line (46). FIG. 4-3 is an optical path diagram illustrating how three points (left-edge-point, mid-point and right-edge-point) on camera's scan-line (46) are illuminated by lights in many directions from line-light (43) as shown in FIG. 4-1. Obviously any point on camera's scan-line (46) will be spread by lights from various directions from the line-light (43). When the light beam (45) pass through the glass panel (41), it will also pass through the lacks and lacks will be exposed. And the line-scan camera (42) photographs line by line and makes a clear side-crash and lacks picture.

This invention introduces an apparatus and method thereof to get clear crack photographs using one line-light. FIG. 5-1 is a schematic diagram illustrating the hardware configuration for crack inspection apparatus according to the present invention and FIG. 5-2 is a schematic diagram illustrating the angle between the glass and the light-beam is 40°~60° according to FIG. 5-1. The line-scan camera (52) is mounted on the backside of glass panel (51) vertically with the glass panel (51), and one line-light (53) is mounted on the backside of glass panel in parallel with camera's scan line (56), and spreads light beam (55) merging with the camera's scan-line (56). FIG. 5-3 is an optical path diagram illustrating how three points (left-edge-point, mid-point and right-edge-point) on camera's scan-line (56) are illuminated by lights in many directions from line-light (53) as shown in FIG. 5-1. Obviously any point on camera's scan line (56) will be spread by lights from various directions from the line-light (53). When the light beam (55) pass through the glass panel (51), will also pass through the cracks and crack's edges will be exposed clearly. And the line-scan camera (52) photographs line by line and makes a clear crack picture.

Figures 1, 2, 3, 6:
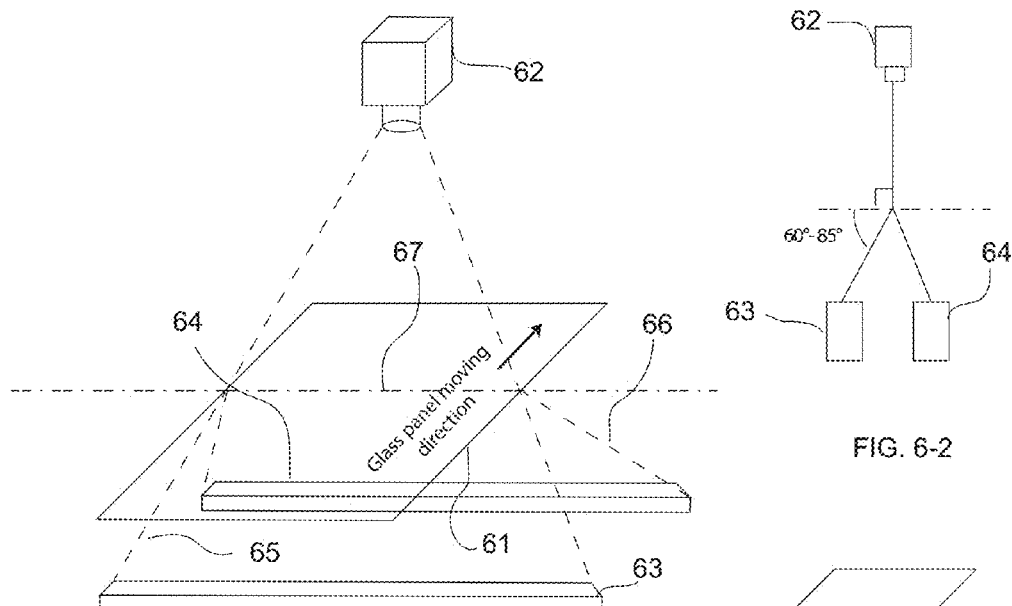

This invention introduces an apparatus and method thereof to get clear pin-hole photographs using two line-lights. FIG. 6-1 is a schematic diagram illustrating the hardware configuration for pin-hole inspection apparatus according to the present invention and FIG. 6-2 is a schematic diagram illustrating the angle between the glass and the light-beams is 60°~85° according to FIG. 6-1. The line-scan camera (62) is mounted on the top of glass panel (61) vertically with the glass panel (61), and two line-lights (63 & 64) are mounted on the backside of glass panel in parallel with camera's scan line (67), and spreads light beams (65 & 66) with the camera's scan-line (67). FIG. 6-3 is an optical path diagram illustrating how three points (left-edge-point, mid-point and right-edge-point) on camera's scan-line (67) are illuminated by lights in many directions from line-lights (63 & 64) as shown in FIG. 6-1. Obviously any point on camera's scan line (67) will be spread by lights from various directions from the line-lights (63 & 64). When the light beams (65 & 66) pass through the glass panel (61), they will also pass through the pin-hole and pin-hole will be exposed. Since some pin-holes are tiny, it is not bright enough to use only one line-light and two line-lights are used. And the line-scan camera (62) photographs line by line and makes a clear pin-hole picture.

This invention introduces an apparatus and method thereof to get clear concave and raised edge photographs using one light. FIG. 7-1 is a schematic diagram illustrating the hardware configuration for concave and raised edge inspection apparatus according to the present invention and FIG. 7-2 is a schematic diagram illustrating the angle between the glass and the light-beam is 70°~80° according to FIG. 7-1. The line-scan camera (72) is mounted on the backside of glass panel (71) vertically with the glass panel (71), and one line-light (73) is mounted on the backside of glass panel (71) in parallel with camera's scan line (75), and spreads light beam (74) merging with the camera's scan-line (75). FIG. 7-3 is an optical path diagram illustrating how three points (left-edge-point, mid-point and right-edge-point) on camera's scan-line (75) are illuminated by lights in many directions from line-light (73) as shown in FIG. 7-1. Obviously any point on camera's scan-line (75) will be spread by lights from various directions from the line-light (73), and concave and raised edge will be exposed clearly. And the line-scan camera (72) photographs line by line and makes a clear concave and raised edge.

This invention introduces an apparatus and method thereof to get clear bubble and smudge photographs using two line-lights. FIG. 8-1 is a schematic diagram illustrating the hardware configuration for bubble and smudge inspection apparatus according to the present invention; and FIG. 8-2 is a schematic diagram illustrating the angle between the glass panel and the topside and backside light beams is 50°~70° and 60°~80° respectively according to FIG. 8-1. FIG. 8-3 is an optical path diagram illustrating how three points (left-edge-point, mid-point and right-edge-point) on camera's scan-line (87) are illuminated by lights in many directions from line-lights (83 & 84) as shown in FIG. 8-1. The camera (82) is mounted at the top of the glass panel (81) vertically with the glass panel (81) and the two line-lights (83 & 84) are mounted at the top and back side of the glass panel respectively and spread line beams (85 & 86) which merge at the camera's scan line (87). Obviously any point on camera's scan line (87) will be spread by lights from various directions from the line-lights (83 & 84), thus it will guarantee all the bubble and smudge defects (in any orientation) be exposed, when the line-scan camera (82) photographs line by line and make a clear bubble and smudge defect picture.

What is claimed is:

1. An apparatus for photographing glass(es) to expose defects, comprising: at least one camera, at least one light source, at least one computer and/or a conveyor;

wherein said defects comprising of one or more of the following types: scratches, silk print defects, black/white defects, lacks, cracks, pin-holes, concave and raised edges, bubbles and smudges on the surface, backside or/and mid-layer of the glass(es);

wherein the angle and distance between said glass and said light sources is designed based on the type of said defects;

wherein the angle and distance between said glass(es) and at least one cameras is designed based on the type of said defects; and wherein said camera is mounted vertically with said glass(es); first two line-lights are mounted in parallel to said camera's scan-line and spread first two line beams on said camera's scan-line; another two line-lights are mounted vertically to said camera's scan-line and spread another two line beams from both sides of said camera; said first two line-lights spread said first two line beams on said camera's scan-line, the angle between said first two light beams and said glass(es) is 70°~80°; said another two line-lights spread said another two line beams from both sides of the camera, the angle between said another two line beams and said camera's scan-line is 20°~30°; and said apparatus is able to take clear photographs for exposing said scratches in all orientation on said glass(es).

* * * * *